United States Patent
Wang et al.

(10) Patent No.: US 11,448,633 B2
(45) Date of Patent: Sep. 20, 2022

(54) TEST DEVICE FOR SIMULATING POLLUTANT MIGRATION AND TRANSFORMATION IN ICING AND MELTING PROCESSES OF WATER BODY

(71) Applicant: Chinese Research Academy of Environmental Sciences, Beijing (CN)

(72) Inventors: Shuhang Wang, Beijing (CN); Bo Zhang, Beijing (CN); Xia Jiang, Beijing (CN); Wenwen Wang, Beijing (CN); Yunyan Guo, Beijing (CN); Li Zhao, Beijing (CN); Junyi Chen, Beijing (CN); Qing Cai, Beijing (CN)

(73) Assignee: Chinese Research Academy of Environmental Sciences, Beijing (CN)

( * ) Notice: Subject to any disclaimer, the term of this patent is extended or adjusted under 35 U.S.C. 154(b) by 0 days.

(21) Appl. No.: 17/149,977

(22) Filed: Jan. 15, 2021

(65) Prior Publication Data

US 2021/0223225 A1    Jul. 22, 2021

(30) Foreign Application Priority Data

Jan. 17, 2020  (CN) .......................... 202010050850.8

(51) Int. Cl.
*G01N 33/18* (2006.01)
*G01N 11/02* (2006.01)

(52) U.S. Cl.
CPC ............. *G01N 33/18* (2013.01); *G01N 11/02* (2013.01); *G01N 2033/1873* (2013.01)

(58) Field of Classification Search
CPC ................... G01N 33/18; G01N 11/02; G01N 2033/1873; G01N 33/1826; F25B 5/00; F25B 30/00
(Continued)

(56) References Cited

U.S. PATENT DOCUMENTS 2,370,931 A * 3/1945 Bogin .................. A47G 21/187
62/293

FOREIGN PATENT DOCUMENTS

CN    207197059    * 4/2018
CN    110522324    * 12/2019
(Continued)

*Primary Examiner* — Robert R Raevis

(57) ABSTRACT

The invention relates to the technical field of test equipment, in particular to a test device for simulating pollutant migration and transformation in icing and melting processes of a water body. The device comprises: a transparent cylinder body with the top open and the bottom closed, used for holding a test water body; a transparent box body, wherein the top of the box body is provided with a through hole through which the cylinder body is provided in the box body; a first refrigerating system including a first evaporator provided in the cylinder body close to an opening of the cylinder body, wherein the first refrigerating system is used for controlling the temperature of a first space from a surface of a test water body in the cylinder body to the opening of the cylinder body through the first evaporator; and a second refrigerating system used for controlling the temperature in the box body. According to the test device provided by the embodiment of the invention, the icing and melting processes of a test water body can be simulated, so that researchers do not need to extract a water sample on site, but can easily know the influence of the icing and melting processes on the migration and transformation of pollutants.

6 Claims, 1 Drawing Sheet

(58) Field of Classification Search
USPC ............ 73/170.29, 53.01, 865.6, 865.8, 866;
62/125, 126, 129, 130, 331, 332, 335,
62/498–512; 374/142–147
See application file for complete search history.

(56) References Cited

FOREIGN PATENT DOCUMENTS

| | | | |
|---|---|---|---|
| JP | 0730023 | * | 1/1995 |
| WO | 2016053160 | * | 4/2016 |

* cited by examiner

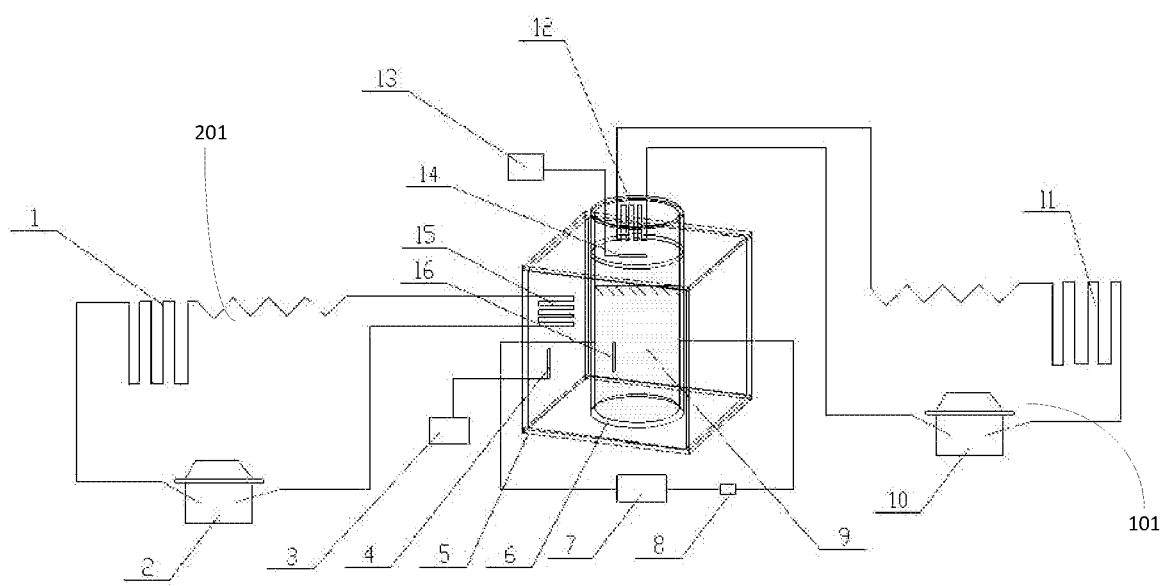

TEST DEVICE FOR SIMULATING POLLUTANT MIGRATION AND TRANSFORMATION IN ICING AND MELTING PROCESSES OF WATER BODY

FIELD OF THE INVENTION

The invention relates to the technical field of test equipment, in particular to a test device for simulating pollutant migration and transformation in icing and melting processes of a water body.

BACKGROUND OF THE INVENTION

Water bodies such as rivers, lakes, oceans and the like have important resource functions, ecological functions and economic functions, and are closely related to production and life of human beings.

In recent years, the water quality of lakes in high latitude cold areas has been decreasing mainly due to the condensation of some indexes including water ions, nutrients, heavy metals and so on, which are caused by the reduction of water quantity and the icebound. Previous researches on lakes were mainly carried out at normal temperature, but in the process of icebound in the high latitude cold area, research works on the substance concentration of ice layer, ice-water interface, water body and sediment during migration and transformation are rarely seen. More and more researches indicate that the change of icebound period has a special effect on the migration of pollutants in water and sediment. Therefore, it is of great practical significance to provide data support for the prevention and control of water pollution during the period of icebound and pollutant migration and transformation during the period of emergence and extinction.

However, according to the traditional research methods, in general, it is extremely difficult for researchers to collect water body and sediment samples during the period of icebound. acquiring ice samples with ice drills is also a tough work, and it is hard, time-consuming and labor-consuming. Moreover, in the process of icing and melting, it should be more difficult to collect samples. All of these increase the cost and difficulty of the investigation. Therefore, there is an urgent requirement for a test device that can simulate pollutant migration and transformation in icing and melting processes of a water body.

SUMMARY OF THE INVENTION

To solve the technical problem, the invention mainly aims at providing a test device with a novel structure for simulating pollutant migration and transformation in icing and melting processes of a water body.

The object and the technical problem to be solved by the present invention are achieved by the following technical solutions. The invention provides a test device for simulating pollutant migration and transformation in icing and melting processes of a water body. The device includes a transparent cylinder body with the top open and the bottom closed, used for holding a test water body;

a transparent box body, wherein the top of the box body is provided with a through hole through which the cylinder body is provided in the box body;

a first refrigerating system including a first evaporator provided in the cylinder body close to an opening of the cylinder body, wherein the first refrigerating system is used for controlling the temperature of a first space from a surface of a test water body in the cylinder body to the opening of the cylinder body through the first evaporator; and a second refrigerating system used for controlling the internal temperature of the box body.

The object and the technical problem to be solved by the present invention are further achieved by the following technical measures.

Optionally, with regard to the afore-mentioned test device for simulating pollutant migration and transformation in icing and melting processes of a water body, the first refrigerating system further comprises a first condenser, a first compressor, a first temperature sensor and a first temperature controller; wherein the first condenser and the first compressor are connected with the first evaporator in series through pipelines, the first temperature sensor is connected with the first temperature controller, the first temperature sensor is used for detecting the temperature of the first space and sending a corresponding first temperature signal to the first temperature controller, and the first temperature controller is connected with the first compressor and used for controlling operation of the first compressor based on the first temperature signal.

Optionally, with regard to the afore-mentioned test device for simulating pollutant migration and transformation in icing and melting processes of a water body, the first temperature sensor is disposed proximate a surface of the test water body within the cylinder body.

Optionally, with regard to the afore-mentioned test device for simulating pollutant migration and transformation in icing and melting processes of a water body, the second refrigerating system comprises a second evaporator, a second condenser, a second compressor, a second temperature sensor and a second temperature controller connected in series through pipelines; wherein the second evaporator is provided inside the box body, the second temperature sensor is connected with the second temperature controller, the second temperature sensor is used for detecting the internal temperature of the box body and sending a corresponding second temperature signal to the second temperature controller, and the second temperature controller is connected with the second compressor and used for controlling operation of the second compressor based on the second temperature signal.

Optionally, with regard to the afore-mentioned test device for simulating pollutant migration and transformation in icing and melting processes of a water body, the second evaporator is provided at the middle of the inner wall of the box body and the outer wall of the cylinder body, and the second evaporator is provided at the middle of the height direction of the box body;

the second temperature sensor is provided at a position between the inner wall of the box body and the outer wall of the cylinder body.

Optionally, with regard to the afore-mentioned test device for simulating pollutant migration and transformation in icing and melting processes of a water body, the second evaporators has a plurality of ones, and the plurality of the second evaporators are provided around the cylinder body and are uniformly distributed in the box body at intervals.

Optionally, the afore-mentioned test device for simulating pollutant migration and transformation in icing and melting processes of a water body further comprises:

a circulation loop including a water pump, and two ends of the water pump are respectively connected with two opposite sides of the cylinder body through water pipes and communicated with the interior of the cylinder body; wherein the water pump is used for driving the test water body in the cylinder body to flow in the circulation loop.

Optionally, the afore-mentioned test device for simulating pollutant migration and transformation in icing and melting processes of a water body further comprises:

the circulation loop further comprises a flow meter connected in series in the water pipe and used for monitoring a water flow rate in the water pipe.

Optionally, the afore-mentioned test device for simulating pollutant migration and transformation in icing and melting processes of a water body further comprises:

a third temperature sensor provided in the cylinder body at a position close to the bottom of the cylinder body, used for being soaked in the test water body and detecting the temperature of the test water body.

Optionally, with regard to the afore-mentioned test device for simulating pollutant migration and transformation in icing and melting processes of a water body, a side wall of the cylinder body is provided with scale marks from the opening to the bottom.

Optionally, the afore-mentioned test device for simulating pollutant migration and transformation in icing and melting processes of a water body further comprises:

a cap body detachably covered on the opening of the cylinder body.

By means of the technical solution, the test device for simulating pollutant migration and transformation in icing and melting processes of a water body has at least the following advantages:

according to the test device for simulating pollutant migration and transformation in icing and melting processes of a water body provided by the embodiment of the invention, the cylinder body can hold the test water body; a first evaporator of a first refrigerating system is provided at a position where the interior of the cylinder body is close to the opening; temperature of the space above the test water body in the cylinder body can be controlled through the first evaporator, that is, the environment temperature during the icing and the melting of the water body in the real environment can be simulated, and the test water body can be gradually iced or gradually ice-melted in the cylinder body to simulate icing and melting of the test water body. In addition, the box body is sleeved outside the cylinder body and is provided with a second refrigerating system, the temperature inside the box body can be adjusted through the second refrigerating system, the water temperature of the test water body is kept consistent with the temperature inside the box body, so that the test water body does not exchange heat with the environment outside, and the simulation of icing and melting of the test water body is closer to the icing and melting of the test water body in the real environment. Therefore, depending on the test device for simulating pollutant migration and transformation in icing and melting processes of a water body, the icing and melting processes of rivers, lakes, oceans and the like can be simulated through tests for the water body, and the icing and melting velocities of the test water body under simulation conditions can be obtained; samples of the test water body may be collected at any stage during the test, and the concentration of pollutants can be detected, furthermore, the migration and transformation of pollutants in the icing or the melting process of the test water body can be known, so that researchers do not need to extract water samples on site, and the researchers can conveniently know the influence of the icing and the melting processes on the migration and transformation of the pollutants.

The above description is merely an outline of the technical solution of the present invention. In order to understand the technical solutions more clearly and implement the device in accordance with the contents of the description, a preferred embodiment of the present invention will be described in detail with reference to the accompanying drawings.

BRIEF DESCRIPTION OF THE DRAWINGS

FIG. 1 is a schematic view showing a structure of a test device for simulating pollutant migration and transformation in icing and melting processes of a water body according to an embodiment of the present invention.

Reference numerals in FIG. 1 correspond to:

101—first refrigerating system, 201—second refrigerating system, 1—second condenser, 2—second compressor, 3—second thermostat, 4—second temperature sensor, 5—box body, 6—cylinder body, 7—water pump, 8—flow meter, 9—test water body, 10—first compressor, 11—first condenser, 12—first evaporator, 13—first temperature controller, 14—first temperature sensor, 15—second evaporator, 16—third temperature sensor.

DETAILED DESCRIPTION OF THE INVENTION

In order to further illustrate the technical solutions and efficacy of the present invention for achieving the intended purposes thereof, reference is now made to the accompanying drawings and preferred embodiments for the following detailed description of a test device for simulating pollutant migration and transformation in icing and melting processes of a water body provided by the invention, its embodiments, structure, features and efficacy. In the following, different "one embodiment" or "an embodiment" refers not necessarily to the same embodiment. Furthermore, the particular features, structures, or characteristics of one or more embodiments may be combined in any suitable form.

As shown in FIG. 1, the invention provides a test device for simulating pollutant migration and transformation in icing and melting processes of a water body, which comprises a transparent cylinder body 6, a transparent box body 5, a first refrigerating system 101 and a second refrigerating system 201; wherein the transparent cylinder body 6 is top open and bottom closed, and used for holding a test water body 9; the top of the box body 5 is provided with a through hole through which the cylinder body 6 is provided in the box body 5; the first refrigerating system 101 includes a first evaporator 12 provided in the cylinder body 6 close to an opening of the cylinder body 6, wherein the first refrigerating system 101 is used for controlling the temperature of a first space from a surface of a test water body 9 in the cylinder body 6 to the opening of the cylinder body 6 through the first evaporator 12; and the second refrigerating system 201 is used for controlling the temperature in the box body 5.

Specifically, the transparent cylinder body 6 may be made of acrylic, or may be made of glass resistant to low temperatures. The cylinder body 6 is preferably a cylindrical cylinder body 6 whose diameter and height may be specifically set according to the requirements of the simulation test. The test water body 9 hold in the cylinder body 6 may be a water sample from a river, lake or ocean to be researched. It should be noted that when a simulation test is carried out, there should not be an excessive amount of the test water body 9 hold in the cylinder body 6, and the water surface of the test water body 9 is spaced from the opening of the cylinder body 6 to avoid contact with the first evaporator 12 of the first refrigerating system 101.

The transparent box body 5 and the transparent cylinder body 6 can be made of the same materials, for example, acrylic materials or low-temperature-resistant glass materials, the shape of the box body 5 can be a cuboid, a cube or a cylinder, and a certain space can be reserved between the cylinder body 6 and the outer wall of the cylinder body 6. The top through hole of the box body 5 can be formed by completely removing the top wall of the box body 5, preferably a circular through hole is formed in the top wall, the diameter of the through hole is in clearance fit with the outer diameter of the cylinder body 6, and excessive air in the box body 5 is prevented from exchanging heat with the air outside.

Reference can be made to appliances such as a refrigerator, an air conditioner and the like for the operating principle of the first refrigerating system 101, and the refrigerating component of the first refrigerating system 101 is a first evaporator 12 that can remove heat from its surroundings and reduce the ambient temperature of its surroundings to achieve a refrigeration effect. The first evaporator 12 is provided in the cylinder body 6 at a position close to the opening of the cylinder body 6, and the first evaporator 12 can be suspended in the cylinder body 6 through a metal pipeline, or can be provided in the cylinder body 6 through a bracket, or can be adhered to the inner wall of the cylinder body 6 through heat insulation adhesive, so that the temperature in the cylinder body 6 is controlled through the first evaporator 12, the first refrigerating system 101 can start to operate after the test water body 9 is held in the cylinder body 6, the temperature of the space from the water surface of the test water body 9 in the cylinder body 6 to the opening of the cylinder body 6 is reduced to the test temperature through the first evaporator 12, and then a simulation test of icing or melting of the test water body 9 is carried out. The space from the surface of the test water body 9 in the cylinder body 6 to the opening of the cylinder body 6 is referred to as a first space.

The operating principle of the second refrigerating system 201 and the first refrigerating system 101 as well as the device provided thereby can be the same and will not be described in detail herein, so long as the second refrigerating system 201 can control the temperature in the box body 5, wherein the control refers to reducing the temperature to the same temperature as the test water body 9 in the cylinder body 6, for example, the temperature of the ice-water mixture, so that the test water body 9 in the cylinder body 6 is prevented from exchanging heat with the outside.

In addition, operation of the first refrigerating system 101 and the second refrigerating system 201 can be controlled by a manual switch or by a terminal device connected thereto. Similarly, the temperature in the cylinder body 6 and the temperature in the box body 5 can be measured manually, the temperature in the cylinder body 6 and the temperature in the box body 5 can be detected in real time by arranging a temperature sensor, the detected temperature of the temperature sensor can be further transmitted to a terminal device, the temperature can be read through the terminal device, and the operation of the first refrigerating system 101 and the second refrigerating system 201 can be controlled.

According to the test device for simulating pollutant migration and transformation in icing and melting processes of a water body provided by the embodiment of the invention, the cylinder body 6 can hold the test water body 9, a first evaporator 12 of a first refrigerating system 101 is provided at a position where the interior of the cylinder body 6 is close to the opening; temperature of the space above the test water body 9 in the cylinder body 6 can be controlled through the first evaporator 12, that is, the environment temperature during the icing and the melting of the water body 9 in the real environment can be simulated, and the test water body 9 can be gradually iced or gradually ice-melted in the cylinder body 6 to simulate icing and melting of the test water body 9. In addition, the box body 5 is sleeved outside the cylinder body 6 and provided with the second refrigerating system 201, the temperature inside the box body 5 can be adjusted through the second refrigerating system 201, the water temperature of the test water body 9 is kept consistent with the temperature inside the box body 5, so that the test water body 9 does not exchange heat with the environment outside, and the simulation of icing and melting of the test water body 9 is closer to the icing and melting of the test water body in the real environment. Therefore, through the test device for simulating pollutant migration and transformation in icing and melting processes of a water body, the icing and melting processes of rivers, lakes, oceans and the like can be simulated through tests for the water body 9, and the icing and melting velocities of the test water body 9 under simulation conditions can be obtained; samples of the test water body 9 may be collected at any stage during the test, and the concentration of pollutants can be detected, furthermore, the migration and transformation of pollutants in the icing or the melting process of the test water body 9 can be known, so that researchers do not need to extract water samples on site, and the researchers can conveniently know the influence of the icing and the melting processes on the migration and transformation of the pollutants.

In a particular embodiment, the first refrigerating system 101 is structured specifically as follows: the first refrigerating system 101 further comprises a first condenser 11, a first compressor 10, a first temperature sensor 14 and a first temperature controller 13; the first condenser 11 and the first compressor 10 are connected in series with the first evaporator 12 through pipelines, the first temperature sensor 14 is connected with the first temperature controller 13, the first temperature sensor 14 is used for detecting the temperature of the first space and sending corresponding first temperature signals to the first temperature controller 13, and the first temperature controller is connected with the first compressor 10 and used for controlling the operation of the first compressor 10 based on the first temperature signals. Reference can be made to the operating principle of a refrigerator for that of the first refrigerating system 101, which will not be described in detail herein.

Specifically, the first condenser 11, the first compressor 10 and the first temperature controller 13 are all provided outside the box body 5, and the first condenser 11 and the first compressor 10 are required to be at a certain distance from the box body 5 to avoid the influence of heat transfer. To be specific, the first condenser 11 and the first compressor 10 can be led out of the box body 5 through the arrangement of pipelines, and are led out of the box body 5 through the wire connection to the first temperature controller 13. The first temperature controller 13 may be provided independently or may be a temperature controller provided with the first compressor 10 itself, so long as the first compressor 10 can be controlled to operate according to a temperature signal detected by the first temperature sensor 14, and the specific control mode and signal transmission mode are known to a person skilled in the art and will not be described in detail herein. The first temperature controller 13 can control operation of the first compressor 10 as set by a researcher and according to the signal of the first temperature sensor 14, for example, the researcher can set the temperature at −10° C. through the first temperature controller 13, then the first temperature controller 13 can obtain the temperature of the first space through real-time detection of the first temperature sensor 14, and if the temperature does not reach −10° C., the first compressor 10 is controlled to operate, otherwise, the first compressor 10 is controlled to stop operating.

Further, the first temperature sensor 14 is provided at a position close to the surface of the test water body 9 in the cylinder body 6.

Specifically, in order to make the simulation test closer to the actual icing or melting of the water body, the first temperature sensor 14 is disposed close to the surface of the test water body 9, so that the ambient temperature at which the test water body 9 is located can be controlled relatively accurately. The first temperature sensor 14 can be suspended at a proper position of the cylinder body 6 in a wire pulling mode, and the setting position can be adjusted according to the height of the surface of the test water body 9.

In a particular embodiment, the second refrigerating system 201 is structured specifically as follows: the second refrigerating system 201 includes a second evaporator 15, a second condenser 1, a second compressor 2, a second temperature sensor 4 and a second temperature controller 3 connected in series through pipelines; the second evaporator 15 is provided inside the box body 5, the second temperature sensor 4 is connected with the second temperature controller 3, the second temperature sensor 4 is used for detecting the internal temperature of the box body 5 and sending a corresponding second temperature signal to the second temperature controller 3, and the second temperature controller is connected with the second compressor 2 and used for controlling the operation of the second compressor 2 based on the second temperature signal. Reference can be made to the operating principle of a refrigerator for that of the second refrigerating system 201, which will not be described in detail herein.

Specifically, the second condenser 1, the second compressor 2 and the second temperature controller 3 are all provided outside the box body 5, and the second condenser 1 and the second compressor 2 need to be at a certain distance from the box body 5 to avoid the influence of heat transfer. To be specific, the second condenser 1 and the second compressor 2 can be led out of the box body 5 through arrangement of pipelines, and the second condenser 1 and the second compressor 2 are led out of the box body 5 through wire connection with the second temperature controller 3. The second temperature controller 3 can be an independent temperature controller or a temperature controller provided with the second compressor 2, so long as the operation of the second compressor 2 can be controlled according to a temperature signal detected by the second temperature sensor 4, and the specific control mode and signal transmission mode are known to a person skilled in the art and will not be described in detail herein. The second temperature controller 3 can control operation of the second compressor 2 as set by a researcher and according to the signal of the second temperature sensor 4, for example, the researcher can set the temperature at 4° C. through the second temperature controller 3, then the second temperature controller 3 can obtain the temperature in the box body 5 through real-time detection of the second temperature sensor 4, and if the temperature does not reach 4° C., the second compressor 2 is controlled to operate, otherwise, the second compressor 2 is controlled to stop operating.

Further, the second evaporator 15 is provided in the middle of the inner wall of the box body 5 and the outer wall of the cylinder body 6, and the second evaporator 15 is provided in the middle of the box body 5 in the height direction; and the second temperature sensor 4 is provided at the position between the inner wall of the box body 5 and the outer wall of the cylinder body 6. Specifically, by arranging the second evaporator 15 at the above-mentioned position in the box body 5, the relative uniformity of the temperature in the box body 5 can be ensured, and a large temperature difference between the upper and lower spaces in the box body 5 caused by the sediment of the cold air is avoided. The second evaporator 15 may be provided in the case 5 through a bracket, may be suspended in the case 5 through a sling, or may be provided in another achievable manner, and the present invention is not limited thereto.

Further, in order to further ensure that the temperatures at various positions in the box body 5 are the same, the second evaporators 15 may be set to have a plurality of ones, and the plurality of the second evaporators 15 are distributed uniformly around the cylinder body 6 in the box body 5 at intervals.

In a particular embodiment, the test device for simulating pollutant migration and transformation in icing and melting processes of a water body further comprises: a circulation loop including a water pump 7, and two ends of the water pump 7 are respectively connected with two opposite sides of the cylinder body 6 through water pipes and communicated with the interior of the cylinder body 6; the water pump 7 is used for driving the test water body 9 in the cylinder body 6 to flow in the circulation loop.

Further, the circulation loop further comprises a flow meter 8 connected in series in the water pipe for monitoring the water flow rate in the water pipe.

Specifically, the water pipe in the circulation loop is preferably made of a plastic material having a low thermal conductivity, and is preferably a flexible pipe in order to facilitate the arrangement of the water pipes. The water pump 7 is preferably adjustable in power or rotational velocity so that the rate of circulation of the test water body 9 can be adjusted, and the specific flow rate of the test water body 9 is known by reading the flow meter 8, and the output power of the water pump 7 is adjusted accordingly to adjust the flow rate of the test water body 9.

The test water body 9 in the cylinder body 6 can circularly flow through the arrangement of the circulation loop, the flow rate of the water body can be known through the monitoring of the flow meter 8, and the test water body 9 can simulate the actual flowing state of water, namely icing and melting in the flowing state of the water.

In a particular embodiment, the test device for simulating pollutant migration and transformation in icing and melting processes of a water body of the invention further comprises: a third temperature sensor 16 provided in the cylinder body 6 close to the bottom of the cylinder body 6 and is used for being soaked in the test water body 9 and detecting the temperature of the test water body 9.

Specifically, the real-time temperature of the test water body 9 can be directly read through the arrangement of the third temperature sensor 16, data are provided for the simulation test, and meanwhile, researchers can adjust test parameters according to the real-time temperature of the test water body 9.

In a particular embodiment, the side wall of the cylinder body 6 is provided with scale marks from the opening to the bottom.

Specifically, through the arrangement of the scale marks and the matching of the box body 5 and the cylinder body 6 in a transparent state, the researchers can visually see the icing thickness of the test water body 9 in the cylinder body 6, or see the remaining thickness upon melting of the test water body 9 after it is iced, for convenience of the observation and the reading of the researchers. In a particular embodiment, a cap body is detachably covered on the opening of the cylinder body 6.

Specifically, the cap body can be rotationally connected or detachably connected with the edge of the opening of the cylinder body 6, preferably is detachably connected, the loss of cold energy in the cylinder body 6 can be reduced through the arrangement of the cap body, and the heat exchange between the air in the cylinder body 6 and the outside through the opening of the cylinder body 6 is reduced.

While the invention has been particularly shown and described with reference to a preferred embodiment thereof, it will be understood by a person skilled in the art that various changes in form and details may be made therein without departing from the spirit and scope of the invention.

What is claimed is:

1. A test device for simulating pollutant migration and transformation in icing and melting processes of a water body, comprising:
    a transparent cylinder body with the top open and the bottom closed, used for holding a test water body;
    a transparent box body, wherein the top of the box body is provided with a through hole through which the cylinder body is provided in the box body;
    a first refrigerating system including a first evaporator provided in the cylinder body close to an opening of the cylinder body, wherein the first refrigerating system is used for controlling the temperature of a first space from a surface of a test water body in the cylinder body to the opening of the cylinder body through the first evaporator; the first refrigerating system further comprises a first condenser, a first compressor, a first temperature sensor and a first temperature controller; the first condenser and the first compressor are connected with the first evaporator in series through pipelines, the first temperature sensor is connected with the first temperature controller, the first temperature sensor is used for detecting the temperature of the first space and sending a corresponding first temperature signal to the first temperature controller, and the first temperature controller is connected with the first compressor and used for controlling operation of the first compressor based on the first temperature signal; the first temperature sensor is provided at a position close to the surface of the test water body in the cylinder body; and
    a second refrigerating system including plurality of second evaporators, a second condenser, a second compressor, a second temperature sensor and a second temperature controller connected in series through pipelines; at least one of the second evaporators inside the box body, the second temperature sensor is connected with the second temperature controller, the second temperature sensor is used for detecting the internal temperature of the box body and sending a corresponding second temperature signal to the second temperature controller, and the second temperature controller is connected with the second compressor and used for controlling operation of the second compressor based on the second temperature signal, wherein the second refrigerating system is used for controlling the internal temperature of the box body;
    a circulation loop including a water pump, and two ends of the water pump are respectively connected with two opposite sides of the cylinder body through water pipes and communicated with the interior of the cylinder body.

2. The test device for simulating pollutant migration and transformation in icing and melting processes of a water body of claim 1, wherein,
    the second evaporators are provided in the middle of an inner wall of the box body and an outer wall of the cylinder body, and are positioned in the middle of a height direction of the box body; and
    the second temperature sensor is provided at a position between the inner wall of the box body and the outer wall of the cylinder body.

3. The test device for simulating pollutant migration and transformation in icing and melting processes of a water body of claim 2, wherein,
    the plurality of the second evaporators are provided around the cylinder body and are uniformly distributed in the box body at intervals.

4. The test device for simulating pollutant migration and transformation in icing and melting processes of a water body of claim 3, wherein,
    the circulation loop further comprises a flow meter connected in series in the water pipe and used for monitoring a water flow rate in the water pipe.

5. The test device for simulating pollutant migration and transformation in icing and melting processes of a water body of claim 4, further comprising:
    a third temperature sensor provided in the cylinder body at a position close to the bottom of the cylinder body, used for being soaked in the test water body and detecting the temperature of the test water body.

6. The test device for simulating pollutant migration and transformation in icing and melting processes of a water body of claim 5, wherein,
    scale marks are provided on a side wall of the cylinder body in the direction from an opening to the bottom.

* * * * *